United States Patent [19]

Wijtsma

[11] Patent Number: 4,839,513
[45] Date of Patent: Jun. 13, 1989

[54] ULTRAVIOLET IRRADIATION DEVICE

[75] Inventor: Jorrit Wijtsma, Drachten, Netherlands

[73] Assignee: U.S. Philips Corporation, New York, N.Y.

[21] Appl. No.: 205,017

[22] Filed: Jun. 6, 1988

Related U.S. Application Data

[63] Continuation of Ser. No. 899,703, Aug. 25, 1986, abandoned.

[30] Foreign Application Priority Data

Sep. 17, 1985 [NL] Netherlands ............... 8502534

[51] Int. Cl.$^4$ ............... A61N 5/00; H01J 61/00
[52] U.S. Cl. ................... 250/504 R; 128/396
[58] Field of Search ........... 250/504 R, 454.1; 128/396, 373; 315/73, 74

[56] References Cited

U.S. PATENT DOCUMENTS

| | | | |
|---|---|---|---|
| 4,013,920 | 3/1977 | Petro | 315/73 |
| 4,298,005 | 11/1981 | Mutzhas | 128/396 |
| 4,305,020 | 12/1981 | Nalepa | 315/73 |
| 4,417,177 | 11/1983 | Damiano | 315/73 |

Primary Examiner—Bruce C. Anderson
Attorney, Agent, or Firm—Norman N. Spain

[57] ABSTRACT

An ultraviolet-radiation emitting device comprises a housing having an opening in one side; a reflector positioned in such housing with its reflecting surface facing such opening; and an ultraviolet radiation source disposed in front of such reflecting surface. A glass plate is secured to such one side of the housing and is adapted to filter out relatively short-wave ultraviolet radiation originating from the radiation source, the glass plate covering the opening in such one side of the housing. The edge of the glass plate, except for a portion thereof, is secured to the housing by means of an adhesive layer. An electrical switch operable to switch off the radiation source, such switch including an actuating element bearing against the inner surface of the glass plate and arranged, upon breakage of the glass plate, to operate such switch, is provided. The actuating element is positioned near the edge portion of the plate such that the non-adhered part of the plate is pushed outwards by the actuating element upon breakage of the plate.

4 Claims, 1 Drawing Sheet

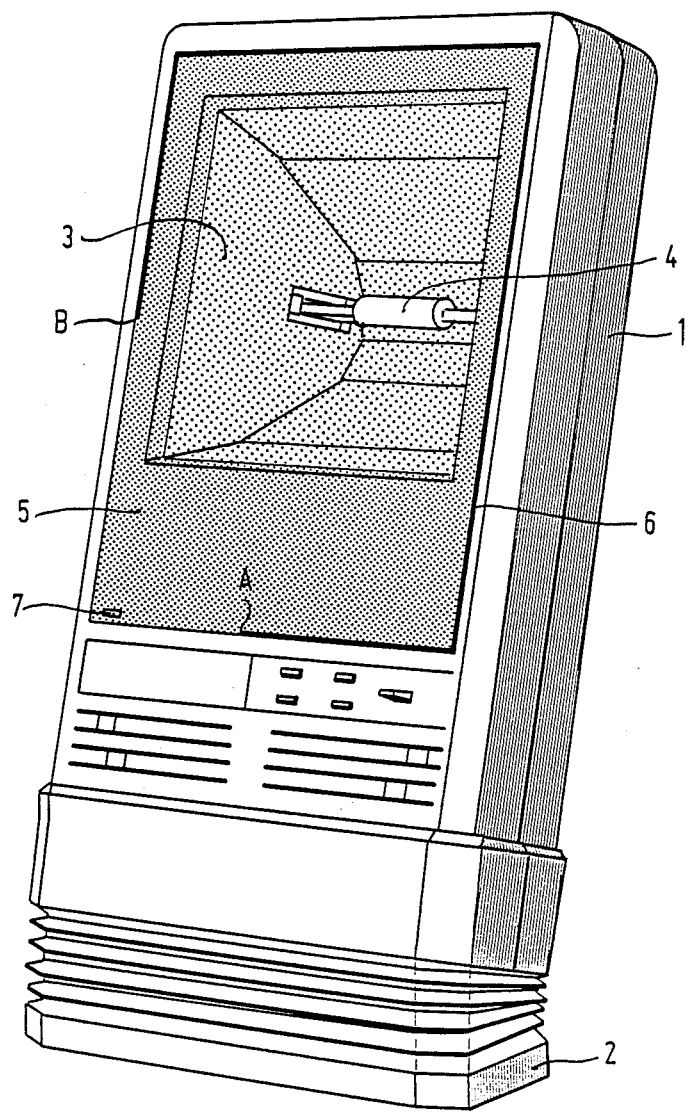

ULTRAVIOLET IRRADIATION DEVICE

This is a continuation of application Ser. No. 899,703, filed Aug. 25, 1986 abandoned.

FIELD OF THE INVENTION

This invention relates to an irradiation device for emitting ultraviolet radiation, having a housing accommodating a reflector in front of which an ultraviolet radiation source is disposed, a glass plate being secured to one side of the housing to filter out relatively short-wave ultraviolet radiation originating from the radiation source, said glass plate covering the radiation exit side of the reflector.

BACKGROUND OF THE INVENTION

A device of this type is commercially available and is used for photobiological purposes, for example, as a facial irradiator for direct pigmentation of the human skin (tanning without erythema) or in phototherapy of dermatological diseases. In this case the body is exposed to long-wave ultraviolet radiation (UV-A radiation) for some time. A relatively small high-pressure metal halide lamp emitting radiation at a wavelength of between about 300 and 400 nm is preferably used as a radiation source in the known device. The glass filter plate positioned in front of the exit side of the reflector passes only UV-A radiation (315–400 nm) whereas UV-B radiation (280–315 nm) originating from the radiation source is obstructed by the plate.

A problem of such known device is that UV-B radiation originating from the radiation source may also emanate if the glass filter plate breaks. This is undesirable, because such radiation may be harmful to the human body.

SUMMARY OF THE INVENTION

The present invention has for its object to provide a device switching off the radiation source as soon as the glass filter plate breaks from any cause whatsoever.

To this end the irradiation device includes an electrical switch operable to switch off the radiation source and having an actuating element which bears against the inner surface of the glass filter plate and which is arranged upon breakage of such glass plate to operate the electrical switch.

In the device according to the invention therefore UV-B radiation is prevented from being released upon breakage of the glass filter plate. The electrical switch may conveniently comprise a push-button switch whose push-button is arranged to bear against the inner surface of the glass plate. In use, the glass plate maintains the button in its depressed state and when the glass filter plate breaks, the pressure of such plate on the button decreases so that it is released, tripping the switch. The radiation source is immediately switched off, because the button is incorporated, for example, in the electrical supply circuit of the radiation source. Preferably the switch's actuating element bears against the glass filter plate outside the radiation exit surface area of the reflector. In that case the actuating element, e.g. the push button is not attacked by the ultraviolet radiation and the heat originating from the radiation source. In addition the radiation efficiency of the device is not adversely affected.

The edge of the glass filter plate is preferably secured to the housing with the aid of a layer of a suitable adhesive, such as a silicone adhesive. In a preferred embodiment the actuating element is provided in a position near a portion of the edge of the glass filter plate adjacent which the adhesive layer is absent over such a distance that the non-adhered glass plate part is pushed outwards by the actuating element upon breakage e.g. cracking of the glass plate, resulting in operation of the switch to switch off the radiation source.

It has been found that in the case of breakage of the glass filter plate only a slight force need be exerted by the actuating element on the glass plate to push it away. This safeguard is therefore very reliable. In addition the electrical switch, e.g. a pushbutton switch, can easily be provided in a position near the edge of the glass plate.

In a special embodiment the glass filter plate is rectangular and has dimensions which are larger than the dimensions of the radiation exit surface area of the reflector. The actuating element is preferably provided in or near one of the corners of the glass filter plate, while the adhesive layer is absent over a maximum distance of half the length of the two side edges of the glass plate defining this corner. In the operative state of the irradiation device the glass filter plate is sufficiently secured while it can quickly be pushed away by the actuating element in the case of breakage.

DESCRIPTION OF THE DRAWING

The invention will now be further described with reference to the accompanying drawing, the single FIGURE of which shows a perspective view of a UV-A table sun lamp suitable for irradiation of the upper part of the body or of the face.

DETAILED DESCRIPTION OF PREFERRED EMBODIMENTS

The irradiation device comprises a synthetic housing 1 placed on a base 2. A user may position the housing 1 in a slightly oblique position relative to the base. The housing accommodates a facetted reflector 3 of anodized aluminum in front of which a radiation source 4 is disposed. The reflector 3 is slightly parabolic. The radiation source is, for example, a high-pressure metal halide lamp having a power rating of 400 W. A transparent glass filter plate 5 adapted to ensure that the relatively short-wave ultraviolet radiation (UV-B radiation and even UV-C radiation) originating from the lamp is absorbed, is positioned on the front side of the housing in front of the reflector. The glass filter plate passes UV-A radiation and some visible light originating from the lamp. The edge of the glass plate is secured to the housing with the aid of an adhesive layer 6. This adhesive layer is shown as a thick solid line in the drawing and consists of a silicone adhesive. A pushbutton switch 7 is present inside the housing 1 and is arranged such that its pushbutton resiliently bears against the inner surface of the glass filter plate 5 near the edge, in a corner, of such plate 5. The switch 7 is connected in the power supply circuit of the lamp 4. The adhesive layer is absent from adjacent portions of the edge of the glass filter plate 5 on either side of the pushbutton over such a distance that the non-adhered part of the glass plate located near the pushbutton is easily pushed outwards by the button upon breakage of the glass plate. In that case the button, previously maintained in its depressed state by the glass filter plate, leaves its depressed state causing the switch to trip, switching off the lamp. The glass filter plate 5 has a rectangular shape. The adhesive layer is absent over a distance measured from the corner near pushbutton switch 7 to the points A and B halfway along the adjacent two edges of the glass filter plate.

The lamp is a high-pressure metal halide lamp (Philips-HPA) whose filling also contains some iron and cobalt. The spectrum of the radiation emitted by the lamp substantially comprises UV-A and UV-B, and some UV-C, radiation in addition to infrared radiation, as well as some visible light.

What is claimed is:

1. An ultraviolet-radiation emitting device, which comprises a housing having an opening in one side; a reflector positioned in such housing with its reflecting surface facing such opening; an ultraviolet radiation source disposed in front of such reflecting surface; a glass plate secured to said one side of the housing and adapted to filter out relatively short-wave ultraviolet radiation originating from the radiation source, said glass plate covering the opening in such one side of the housing, the edge of the glass plate, except for a portion thereof, being secured to the housing by means of an adhesive layer; and, an electrical switch operable to switch off the radiation source, said switch including a depressed actuating element bearing against the inner surface of the glass plate and arranged, upon breakage of the glass plate, to be released from such depressed state to operate said switch; the actuating element being positioned near said non-adhered edge portion of the plate such that the non-adhered part of the plate is pushed outwards by the actuating element upon breakage of the plate and said switch is operated.

2. A device according to claim 1, in which the actuating element bears against the inner surface of the glass plate outside that part covering the housing opening.

3. A device according to claim 2, in which the glass plate is rectangular; and the actuating element is positioned in or near a corner of the plate, the adhesive layer being absent over a maximum distance of half the length of the two side edges of the plate defining said corner.

4. An ultraviolet-radiation emitting device, which comprises a housing having an opening in one side; a reflector positioned in such housing with its reflecting surface facing such opening; an ultraviolet radiation source disposed in front of such reflecting surface; a glass plate secured to said one side of the housing and adapted to filter out relatively short-wave ultraviolet radiation originating from the radiation source, said glass plate covering the opening in such one side of the housing, the edge of the glass plate, except for a portion thereof, being secured to the housing by means of an adhesive layer which is absent over a maximum distance of half the length of the two side edges of the plate defining a non-adhered corner; and, an electrical switch operable to switch off the radiation source, said switch including a depressed actuating element positioned in or near said non-adhered corner, bearing against the inner surface of the glass plate and maintained in said depressed state thereby; said element being arranged, upon breakage of the glass plate, to be released from the depressed state to operate said switch and to push the non-adhered part of the plate outwards upon breakage of the plate.

* * * * *